United States Patent [19]

Kobos et al.

[11] Patent Number: 4,931,172

[45] Date of Patent: Jun. 5, 1990

[54] FLUORIDE ION-SELECTIVE ELECTRODES BASED UPON SUPERIONIC CONDUCTING TERNARY COMPOUNDS AND METHODS OF MAKING

[75] Inventors: Robert K. Kobos; Lorenzo F. Pelosi, both of Wilmington, Del.

[73] Assignee: E. I. Du Pont de Nemours and Company, Wilmington, Del.

[21] Appl. No.: 201,233

[22] Filed: Jun. 2, 1988

[51] Int. Cl.$^5$ .............................................. G01N 27/30
[52] U.S. Cl. ................................................... 204/418
[58] Field of Search ........................ 204/418, 419, 1 B

[56] References Cited

U.S. PATENT DOCUMENTS

| | | | |
|---|---|---|---|
| 3,431,182 | 3/1969 | Frant | 204/1 |
| 3,446,726 | 5/1969 | Pungor et al. | 204/296 |
| 3,787,309 | 1/1974 | Neti et al. | 204/195 M |
| 4,021,325 | 5/1977 | Pungor et al. | 204/195 M |

FOREIGN PATENT DOCUMENTS

| | | |
|---|---|---|
| 0227073 | 1/1987 | European Pat. Off. |
| 5326839 | 8/1974 | Japan |
| 013956 | 4/1977 | Japan |
| 66747 | 6/1981 | Japan |
| 3907 | 1/1982 | Japan |
| 249050 | 10/1987 | Japan |
| 343211 | 7/1972 | U.S.S.R. |
| 989439 | 1/1983 | U.S.S.R. |
| 2163457 | 2/1982 | United Kingdom |

OTHER PUBLICATIONS

Richard A. Durst, "Ion-Selective Electrodes", pp. 89-90, (1969).
Koryta. Anal. Chim. Acta vol. 183, 1-46 (1986).
Arnold and Solsky, Anal. Chem. vol. 58, 84R-101R (1986).
Sher et al., Phys. Rev. vol. 144, 593-604 (1966).
Frant and Ross, Science, vol. 154, 1553-1555 (1966).
Fjeldly and Nagy, J. Electrochem. Soc. 127, 1299-1303 (1980).
Bixler and Solomon, Anal. Chem. 56, 3004-3005 (1984).
McDonald and Toth, Anal. Chim. Acta vol. 41, 99-106 (1968).
Bausova et al., J. Anal. Chem. U.S.S.R. vol. 28, 2042-2044 (1973) (translation only).
Hirata and Ayuzawa, Chem. Lett., 1451-1452 (1974).
Lingane, Anal. Chem., vol. 40, 935-939 (1968).
Moody and Thomas, Ion-Selective Electrodes, 69-70, published by Merrow, England (1971).
Nagel and O'Keefe, Fast Ion Transport in Solids, 165-170, W. van Gool, ed. Elsevier, New York, (1973).
Takahashi et al., J. Electrochem. Soc. vol. 124, 280-284 (1977).
Siddigi, Clin. Chem. vol. 28, 1962-1967, (1982).

Primary Examiner—G. L. Kaplan

[57] ABSTRACT

This invention relates to fluoride ion-selective electrodes which employ, as the active membrane component, a ternary compound of the type $M_xLn_yF_{3-x}$, where M is an alkaline earth metal ion such as calcium, strontium or barium, and Ln is a lanthanide metal ion such as lanthanum, cerium, prosiodymium, neodymium, promethium, samarium and europium.

10 Claims, No Drawings

FLUORIDE ION-SELECTIVE ELECTRODES BASED UPON SUPERIONIC CONDUCTING TERNARY COMPOUNDS AND METHODS OF MAKING

FIELD OF INVENTION

This invention relates to the field of ion-selective electrodes and particularly to the field of fluoride ion-selective electrodes employing supersonic conducting ternary compounds as the active membrane component

BACKGROUND ART

Ion-selective electrodes are electrochemical sensors which respond to the concentration of specific ionic species in sample solution. The principle for measurement is based on the selective permeability of a membrane for specific ionic species in the sample solution. The response of these sensors depends upon the magnitude of the potential developed across an ion-selective membrane which separates two solutions. i.e., an internal reference solution and the sample solution. The membrane acts as an ion-exchanger which selectively takes up the specific ions leaving counterions behind. This separates the charge at the membrane surface inducing a phase boundary potential.

The potential of the ion-selective electrode is measured against an external reference electrode which Provides a fixed potential that is in dependent of any ionic species in the sample solution. An internal reference electrode, which is an integral part of the ion-selective electrode, provides a fixed potential that is determined by the known concentration of the specific ionic species in the internal reference solution. The measured potential is related to the concentration of the specific ionic species in the sample solution by the well known Nernst equation, $$E = Constant - RT/F \ln a_F-$$

where the constant term includes the standard or zero potential of the ion-selective electrode. i.e., the potential of the electrode when the effective concentration is unity; the reference electrode potential; and the junction potential, $a_F-$ is the effective concentration of the specific ions in the sample solution, R is the gas constant(8.316 J/mol-deg), T is the absolute temperature, and $a_F-$ is the Faraday constant (96.491 coulombs). Many authors have described ion-selective electrodes and their use for numerous ionic species [Freiser edited, Ion Selective Electrodes in Analytical Chemistry, Volumes 1 and 2, Plenum Press (1978 and 1980). Koryta, Anal. Chim. Acta Vol. 183, 1–46 (1986), and Arnold and Solsky, Anal. Chem. Vol. 58, 84R–101R (1986)].

The importance of determining fluoride ion concentrations in various Products as well as in natural and biological materials is well known [Moody and Thomas, Ion-Selective Electrodes in Analytical Chemistry, Freiser ed., Plenum Press, Volume 1, 339–433, 1978]. However, conventional analytical techniques such as gravimetric or volumetric methods are tedious and labor intensive. Fluoride ion-selective electrodes have been widely used for both scientific and industrial applications because of their ease of use, reliability, exceptional selectivity and sensitivity. Performance of the ion-selective membranes is affected by various factors such as as the aqueous solubility of the active component, ionic conductivity, seal strength at the contact point with an internal reference solution thermal expansion properties as well as the process by which the membrane is prepared. It is well known in the art that pure crystalline rare earth fluorides have high electrical conductance resulting from mobile fluoride ions within defects in the crystal lattice [Sher et al, Phys. Rev. Vol. 144, 593–604 (1966)]. Many of these crystalline fluorides are also water insoluble which make them ideally suitable for use as membranes in high sensitivity fluoride ion-selective electrodes.

The first fluoride ion-selective electrode employing a non-porous membrane of substantially insoluble crystalline fluoride, i.e., the trifluorides of bismuth, scandium, yttrium and the lanthanide series of rare earth metals, and lead fluoride has been described by Frant and Ross in Science, Vol. 154, 1553–1555 (1966) and by Frant in U.S. Pat. No. 3,431,182 issued on Mar. 4, 1969. The most successful membrane disclosed by Frant is a single-crystal of pure lanthanum trifluoride which has a tysonite structure. The fluoride electrode is prepared by sealing a disk-shaped section of the lanthanum trifluoride crystal into a rigid, polyvinyl chloride tube, which is filled with a solution of sodium fluoride and sodium chloride. Electrical contact is made with a silver/silver chloride reference electrode, which is inserted into the internal reference solution. The single-crystal electrodes have a detection limit of $10^{-6}$M fluoride ions, rapid response time of less than 30 seconds and stable potential measurement capability of 1 mV. These electrodes are useful for various applications but not as single-use sensors for clinical applications because of the high cost involved in membrane preparation. Single crystal membranes require expensive, highly pure optical grade raw materials and time consuming processes. Other problems include tight sealing requirement of the fragile membrane to a variety of sensing electrode configurations and poor thermal expansion properties.

The construction of solid-state fluoride electrodes, in which a silver/silver fluoride contact replaces the internal solution contact, has been reported by Fjeldly and Nagy, J. Electrochem. Soc. 127, 1299–1303 (1980), and Bixler and Solomon, Anal. Chem. 56, 3004–3005 (1984).

There is a need for fluoride electrodes which are of sufficiently low cost to permit them to be used as disposable sensors for clinical applications.

Numerous attempts have been made to prepare such low cost fluoride ion-selective membranes, however, none were successful in overcoming the known disadvantages while maintaining or improving the sensitivity of the single crystal electrodes.

Pungor, et al in U.S. Pat. No. 3,446,726 issued on May 27, 1969 discloses the fabrication of low cost, heterogeneous ion-selective membranes comprising silicone rubber containing small particles of ionic conducting inorganic precipitates. The process was successful for producing silver iodide and barium sulfate membranes. The membranes thus prepared were easily manufacturable, mechanically rigid with great elasticity, resistant to thermodilatation, and highly conductive. However, similar membranes containing polycrystalline fluorides were not disclosed.

An attempt to produce silicone rubber membranes containing powdered lanthanum trifluoride, thorium tetrafluoride, or calcium difluoride has been described by McDonald and Toth in Anal. Chim. Acta Vol. 41, 99–106 (1968). The electrodes thus prepared from lanthanum trifluoride precipitates showed ion selectivity over a narrow range of fluoride ion concentrations from $10^{-4}$ to $10^{-2}$. The most stable fluoride electrode was one prepared with calcium difluoride precipitates. However, sensitivity was poor with a detection limit of $10^{-4}$M. In addition, resistance of these electrodes was very high which requires high impedance electrometers for potential measurement.

Yet another attempt to prepare heterogeneous fluoride electrodes has been disclosed by Radhakrishna et al in U.S. Pat. No. 3,787,309 issued on Jan. 22, 1974. Electrodes in this invention are constructed using a sintered membrane containing insoluble inorganic salts such as lanthanum fluoride incorporated into a polyalkene resin. Sensitivity improved slightly to $5 \times 10^{-5}$M but is not as good as the single crystal lanthanum fluoride electrode.

Still another attempt to produce low cost fluoride electrodes involves a vapor deposition technique which coats a thin layer of polycrystalline lanthanum trifluoride onto a metal or metal-coated base material [Fait et al, GB 2,163,457A issued on Feb. 26, 1982]. Electrodes of this type can be produced by mass fabrication techniques and have good sensitivity down to $1 \times 10^{-5}$M fluoride ions. However, the high resistance of polycrystalline fluoride may require high impedance electrometers, and the potential measurement would be inherently less reliable since it lacks a stable internal reference electrode.

Other attempts directed at improving the performance of the membranes include: use of a spherical shape membrane comprising a single cyrstal fluoride of a lanthanide mixture [Pungor et al, U.S. Pat. No. 4,021,325 issued on May 3, 1977]; use of lanthanum trifluoride doped with europium difluoride [Frant and Ross, Science Vol. 154, 1553-1555 (1966) and Bausova et al, J. Anal. Chem. U.S.S.R. Vol. 28, 2042-2044 (1973)]; use of ceramic membranes comprising a mixture of lanthanum fluoride, europium difluoride and calcium difluoride [Hirata and Ayuzawa, Chem. Lett. 1451-1452 (1974)]; and use of ceramic membranes of sintered cerium fluoride doped with rare earth metals such as europium, samarium or ytterbium [J 77-013,956 issued on Apr. 18, 1977].

Use of a spherical shape membrane eliminated the thermodilatation problem of the single cyrstal electrodes but the cost disadvantage was still high. Ceramic membranes showed high sensitivity and selectivity, comparable to the single-crystal lanthanum fluoride electrode but the processes required high temperature and pressure not easily attainable in manufacturing. The process for preparing these sintered membranes was further complicated by the need to obtain a non-porous structure. In addition. Hirata's process [Chem. Lett. 1451-1452 (1974)] required an atmosphere of corrosive hydrogen fluoride. Although europium doping of lanthanide metal fluorides are known to enhance ionic conductance, the real advantage in such fluoride electrodes is questionable. Doping is accomplished by adding a small amount of europium difluoride, 0.1 to 0.15 mole % which presumably helps to form a nonstoichiometric crystal with holes for fluoride ions to move around. However, europium difluoride is very unstable thus at least in the membrane surface which is exposed to dissolved oxygen in solution, the europium is expected to be in a +3 oxidation state. Then, since the solubility product of europium trifluoride is about ten times larger than that of lanthanum trifluoride, addition of large quantities of europium Would decrease sensitivity of the membrane. [Lingane, Anal. Chem., Vol. 40, 935-939 (1968). Moody and Thomas, Ion-Selective Electrodes, 69-70, published by Merrow, England, 1971].

Supersonic conducting ternary compounds have been known in the art for some time [Nagel and O'Keefe, Fast Ion Transport in Solids, 165-170, W. van Gool, ed. Elsevier, New York, 1973 and Takahashi et al, J. Electrochem. Soc. Vol. 124, 280-284 (1977)]. Supersonic conductors are solids with ion conductances exceeding 0.01 ohm-1 cm-1resulting from the motion of ions, not electrons [Mahan, Superionic Conductors, Mahan and Ross ed., Plenum Press, New York and London, 115, 1976]. These materials have also been called solid electrolytes or fast-ion conductors. The fluoride ion conductors have tysonite-type structure with the general formula, $M_xLn_yF_{3-x}$ where M is an alkaline earth metal ion such as calcium, strontium or barium and Ln is a lanthanide metal ion such as lanthanum or cerium and y equals $1-x$. Conductivity of these ternary fluoride compounds is reported to be about an order of magnitude greater than Pure fluorides of lanthanide metals up to about 5 mole % doping, with the best one known in the art being $Ce_{0.95}Ca_{0.05}F_{2.95}$. The results in these studies supported the earlier hypothesis that mobile fluoride ions in the crystal lattice of large cationic metal fluorides are responsible for the high conductance.

Several reports have appeared recently that describe the use of single crystal fluoride electrodes for measurement of enzyme activities [Siddiqi, Clin. Chem. Vol. 28. 1962-1967 (1982) and EP 0,227,073 issued on Jan. 7, 1987]. The technique is based on the detection of $H_2O_2$(-hydrogen peroxide) produced by various enzymatic reactions such as oxidation of glucose by glucose oxidase. The detection means comprises an interaction of $H_2O_2$ with fluorinated aromatic compounds such as 4-fluoroaniline or 4-fluorophenol in the presence of peroxidase to generate fluoride ions which may then be measured by the fluoride ion-selective electrode. This permits rapid and simple measurements of enzyme activities and their substrates in biological fluids. These disclosures, however, do not teach the use of or how to prepare high sensitivity fluoride electrodes that are of sufficiently low cost as to be especially useful as disposable sensors for clinical applications.

SUMMARY OF THE INVENTION

Many of these difficiencies of the prior art are overcome by this invention which relates to a membrane for use in fluoride ion-selective electrodes comprising a ternary compound of the type, $M_xLn_yF_{3-x}$ where M is an alkaline earth metal ion and Ln is a lanthanide metal ion, as an active component and y equals $1-x$. The membranes may be nonpolymer based and may be formed by vapor depositing the described ternary compound on a suitable inert support. Alternatively, the described ternary compound may be formed into sintered pellet membranes.

In its preferred embodiment, the ternary compound of this invention is used in a fluoride ion-selective electrode for determining the concentration of fluoride ions in a solution to be measured, the electrode having a tube adapted to contain an internal reference solution containing fluoride ions, an internal reference electrode positioned in the tube and adapted to be contacted by the solution, and a diffusion membrane at one end of the tube adapted to function as a diffusion barrier between the solution to be measured and the reference solution, and the invention is the improvement wherein the membrane comprises a ternary compound of the type, $M_xLn_yF_{3-x}$ where M is an alkaline earth metal ion and Ln is a lanthanide metal ion, as the active component and y equals $1-x$. Also included in the invention is a method for making the fluoride ion-selective electrode, in which the membrane is prepared by the steps of: forming a ternary compound of the type, $M_xLn_yF_{3-x}$ where M is an alkaline earth metal ion and Ln is a lanthanide metal ion, as the active component and y equals $1-x$, grinding the ternary compound into particles, and incorporating the particles into a hydrophobic polymer to form a matrix of particles.

Fluoride ion selective electrodes of the ternary compound of this invention are of sufficiently low cost as to permit their use as disposibles and yet provide a high sensitivity. They are suitable for use in clinical applications where disposability is a significant factor.

DETAILED DESCRIPTION OF THE PREFERRED EMBODIMENT

According to the present invention, low cost fluoride ion-selective electrodes are made using superionic fluoride ion conductors as the active component in a polymer diffusion membrane. The supersonic conductors have the general formula, $M_xLn_yF_{3-x}$ where M is an alkaline earth metal ion, i.e.. calcium, strontium or barium, and Ln is a lanthanide metal ion, i.e., lanthanum, cerium, prosiodymium, neodymium, promethium samarium or europium and y equals $1-x$. UP to 15 mol percent of the alkaline earth fluoride can be advantageously utilized in the ternary compound, i.e., $M_{0.15}Ln_{0.85}F_{2.85}$. Membranes are prepared by incorporating from 50 to 90% w/w of the superionic fluoride conductor that has been finely ground and seived, to give particle sizes less than 75 $\mu$m, into a polymer matrix. The polymer can be any chemically inert, hydrophobic polymer. The polymer must be able to hold the particles in intimate contact with each other. Suitable polymers include silicone rubber, poly(tetrafluoroethylene), poly(vinyl chloride), polypropylene, polystyrene, or polyethylene.

In addition to the conventional tubular electrode design, solid-state, planar fluoride electrodes and tubular flow-through electrodes can be readily fabricated using superionic conductor/silicone rubber membranes. Planar electrodes are fabricated by forming the superionic conductor/silicone rubber membrane in a small hole in a silastic sheet. Tubular flow through electrodes are prepared by forming the superionic conductor/silicone rubber membrane in a small hole in the side of silicone rubber tubing.

The preferred embodiment of the invention involves the preparation of fluoride selective membranes by incorporating 80% w/w of a superionic fluoride ion conductor of the type, $M_{0.05}Ln_{0.95}F_{2.95}$, where M is an alkaline earth metal ion such as calcium, strontium or barium, and Ln is lanthanum or cerium. The ternary compound is ground and sieved to give a particle size of less than 75 $\mu$m and preferably less than 40$\mu$ and added to an uncrosslinked silicone rubber such as Siloprene® K1000 so that the superionic fluoride ion conductor composition is 80% by weight. The resulting combination is mixed thoroughly with a mortar and pestle. A crosslinking agent such as Siloprene® K1000 crosslinker is added and the silicone rubber mixture is mixed again. The silicone rubber mixture is transferred to a mold which has a cavity with a thickness of 0.33 to 1.5 mm. After curing, the silicone rubber membrane is removed and cut into circular pieces for use as the fluoride electrode membrane in an otherwise conventional manner. The circular piece is sealed to the end of a piece of silicone tubing using a conventional sealant. The tubing is filled with an internal reference solution containing fluoride ions (a solution of sodium fluoride and sodium chloride is usual). An internal reference electrode is positioned in the tubing to contact the solution. The thickness of the membrane is selected according to the use desired.

The superionic conductor-based fluoride electrodes typically have near-Nernstian response slopes of 55–58 mV/decade down to fluoride ion concentrations of $1\times 10^{-5}$M, with a lower detection limit of $1\times 10^{-6}$M, which are similar to that of the single-crystal lanthanum trifluoride electrode. The selectivity is also similar to the single-crystal electrode, i.e., the only serious interference is from the hydroxide ion. The resistance of the superionic conductor/silicone rubber membranes is surprisingly low, i.e., $10^8$ ohms which is 2–3 orders of magnitude lower than similar membranes prepared with polycrystalline lanthanum trifluoride. Only about a ten fold improvement in the resistance would be expected based on the prior art. The resistance of the suPerionic conductor/silicone rubber electrodes is still much higher than that of the single-crystal lanthanum trifluoride electrode which is approximately $10^5$ ohms. However, this has been shown to have no deleterious effect on their response characteristics in the present invention.

The excellent selectivity and detection limit of the superionic conductor-based fluoride electrodes is unexpected because they contain such a large amount of alkaline earth fluoride, which has a much higher solubility than lanthanum trifluoride. The selectivity and lower detection limit of ion-selective electrodes are highly dependent on the solubility of the active component of the membrane. The addition of a much more soluble component would be expected to adversely affect these response characteristics. For this reason, the amount of Europium difluoride doping used in the single-crystal lanthanum trifluoride electrode is very small [G. J. Moody and J. D. R. Thomas, Ion-Selective Electrodes, Merrow Publishing Co., Watford, England, 1971. pp. 69–70; J. J. Lingane, Anal. Chem. 39. 881 (1967)]. Based on the solubility of calcium difluoride, the lower detection limit of these electrodes would be expected to be only approximately $4\times 10^{-4}$M. The much lower detection limit observed, $1\times 10^{-6}$M, is most likely due to the use of a true ternary compound which has a low solubility. The present invention uses high conductivity ternary metal fluorides for the fabrication of low cost, high sensitivity fluoride ion-selective membranes especially useful as disposable sensors for clinical applications. The method described is extremely simple and reproducible, and allows preparation of the membrane in any desirable form and thickness.

The superionic flouride conductors can also be used to prepare non-polymer-based fluoride selective membranes for fluoride electrodes, e.g., vapor deposited membranes and sintered pellet membranes. Vapor deposited membranes may be prepared by depositing thin layer, e.g., 100 nm of gold or silver on a suitable inert support, such as a polished silicone disc, followed by depositing a thin layer e.g., 270 nm of the ternary compound of this invention at a temperature of more than 200° C.

Sintered pellet membranes may be prepared by mixing the powder of lanthanide metal fluoride with alkaline earth metal fluoride at a given ratio followed by hand pressing them into pellets and calcining at 750° C. or above for at least 4 hours. The pellets are then crushed and ground into fine powder which may be pressure-molded hydrostatically into cylindrical shapes or disks and sintered at 870 to 900° C. The calcining and sintering processes should be performed under an inert gas atmosphere.

EXAMPLE 1

Preparation of a $Ca_{0.15}La_{0.85}F_{2.85}$/Silicone Rubber Fluoride Electrode The ternary compound $Ca_{0.15}La_{0.85}F_{2.85}$ was prepared by mixing commercial powders of $CaF_2$ and $LaF_3$ in the appropriate mole ratio to give a mixture that is 15 mol percent $CaF_2$. The mixture was heated in an inert atmosphere to a temperature greater than 1500° C. to completely melt the mixture. The melt was allowed to cool to room temperature under an inert atmosphere. The resulting ternary compound was ground into fine particles with an Agate mortar and pestle, and passed through a 400 mesh screen to give a particle size of <40 micrometers. The ground melt was examined using X-ray diffraction to verify the presence of a single phase which indicates the formation of a ternary compound.

The fluoride selective, silicone rubber membrane was prepared by intimately mixing 4.0 g of the ternary compound with 1.0 g of Siloprene K1000 silicone rubber (Fluka Chemicals) with an Agate mortar and pestle. The mixture was allowed to de-gas under vacuum and then 0.1 g of Siloprene K1000 cross-linker was added. The cross-linker was carefully mixed into the siloprene mixture with the mortar and pestle without incorporating excess air. This mixture was quickly transferred into a small, two-part Lucite® or Teflon® mold for curing. The mold had a 1.3 mm (50 mil) thick by 1.5 inch diameter circular cavity. During the curing process, the mold was placed in a press at room temperature under slight pressure to squeeze-out excess Siloprene. The mixture was allowed to cure for at least 30 minutes. After this time, the cured wafer was removed from the mold and cut into 8 mm circular discs. The fluoride electrode was prepared by sealing a circular piece (8 mm diameter) of the silicone rubber membrane onto a short piece (8–10 cm) of silicone rubber tubing (external diameter 8 mm) using a commercial silicone sealant. The sealant was allowed to dry overnight, after which the inside of the tubing was filled with a solution containing 0.01 M sodium fluoride and sodium chloride. A silver/silver chloride wire was inserted into the internal solution to complete the electrode.

The resistance of the membrane and the potential of the fluoride electrode, versus a saturated calomel electrode, was measured using a high input impedance electrometer (Keithley model 616). Electrodes that were tested immediately had a resistance of $10^{10}$ ohms. After soaking in distilled water overnight, the resistance dropped to $10^8$ ohms. In comparison electrodes prepared in the same manner using lanthanum trifluoride melts or ground lanthanum trifluoride single-crystals had a resistance that was too high to measure immediately. The resistance of these electrodes dropped to $10^{10}$ to $10^{11}$ to ohms after soaking in water overnight. The high resistance of these electrodes required that measurements be made in a Faraday cage to reduce capacitive noise. In addition, electrodes prepared from a physical mixture of $LaF_3$ and $CaF_2$ in the same mole ratio in which a ternary compound was not formed, had resistances that were similar to that of the pure lanthanum trifluoride membranes.

The fluoride response of the superionic conductor electrode was tested by placing the electrode, along with the reference electrode, into 25.0 mL of total ionic strength adjusting buffer (TISAB), prepared by placing 57 mL of glacial acetic acid and 58 g of sodium chloride into distilled-deionized water, adjusting the pH to 5.0–5.5 with 5 M sodium hydroxide, and diluting to 2 L with distilled-deionized water. After a stable potential was obtained, additions of 0.1 or 0.01 M NaF were made and the steady-state potentials were recorded. Typical results are shown in Table 1. Also included for comparison, is the response of electrodes prepared as described above using $LaF_3$ melts and ground europium-doped $LaF_3$ single-crystal incorporated into silicone rubber membranes.

TABLE 1

FLUORIDE RESPONSE OF SILICONE RUBBER MEMBRANE ELECTRODES

| | Electrode Potential in mV | | |
|---|---|---|---|
| $[F^-]$ | Superionic Conductor | $LaF_3$ Powder | Ground $LaF_3$ Single Crystal |
| $4.0 \times 10^{-5}$ | 284 | 199 | 210 |
| $1.2 \times 10^{-4}$ | 257 | 185 | 193 |
| $3.2 \times 10^{-4}$ | 233 | 171 | 178 |
| $7.2 \times 10^{-4}$ | 213 | 157 | 162 |
| $1.5 \times 10^{-3}$ | 195 | 144 | 149 |
| $3.4 \times 10^{-3}$ | 174 | 130 | 129 |
| $7.0 \times 10^{-3}$ | 156 | 115 | 109 |
| $1.3 \times 10^{-2}$ | 140 | 99 | 96 |
| slope (mV/decade) | −57.1 | −39.4 | −45.7 |
| Resistance(ohms) | $3.5 \times 10^8$ | $3.9 \times 10^{10}$ | $5.7 \times 10^{10}$ |

This data clearly demonstrates the superior response characteristics of fluoride electrodes prepared using superionic conducting ternary compounds in silicone rubber membranes.

EXAMPLE 2

Preparation of a $Sr_{0.15}La_{0.85}F_{2.85}$/Silicone Rubber Fluoride Electrode The ternary compound $Sr_{0.15}La_{0.85}F_{2.85}$ was prepared as described in Example 1 using a mixture of $SrF_2$ and $LaF_3$. Silicone rubber electrodes using this compound were prepared and tested as described in Example 1. Typical response data is given in Table 2.

TABLE 2

FLUORIDE RESPONSE OF $Sr_{0.15}La_{0.85}F_{2.85}$/SILICONE RUBBER FLUORIDE ELECTRODE

| $[F^-]$ | Potential, mV |
|---|---|
| $4.0 \times 10^{-5}$ | 286 |
| $1.2 \times 10^{-4}$ | 260 |
| $3.2 \times 10^{-4}$ | 235 |
| $7.2 \times 10^{-4}$ | 215 |
| $1.5 \times 10^{-3}$ | 196 |
| $3.4 \times 10^{-3}$ | 175 |
| $7.0 \times 10^{-3}$ | 157 |
| $1.3 \times 10^{-2}$ | 140 |
| Slope (mV/decade) | −58.0 |
| Resistance (ohms) | $2.9 \times 10^8$ |

EXAMPLE 3

Preparation of $Ba_{0.15}La_{0.85}F_{2.85}$ A/Silicone Rubber Fluoride Electrode The ternary compound $Ba_{0.15}La_{0.85}F_{2.85}$ was prepared as described in Example 1 using a mixture of $BaF_2$ and $LaF_3$. Silicone rubber electrodes using this compound were prepared and tested as described in Example 1. Typical response data is given in Table 3.

TABLE 3
FLUORIDE RESPONSE OF $Ba_{0.15}La_{0.85}F_{2.85}$/SILICONE RUBBER FLUORIDE ELECTRODE

| $[F^-]$ | Potential, mV |
|---|---|
| $4.0 \times 10^{-5}$ | 246 |
| $1.2 \times 10^{-4}$ | 220 |
| $3.2 \times 10^{-4}$ | 196 |
| $7.2 \times 10^{-4}$ | 176 |
| $1.5 \times 10^{-3}$ | 157 |
| $3.4 \times 10^{-3}$ | 136 |
| $7.0 \times 10^{-3}$ | 118 |
| $1.3 \times 10^{-2}$ | 101 |
| Slope (mV/decade) | −57.6 |
| Resistance (ohms) | $1.8 \times 10^8$ |

EXAMPLE 4

Preparation of a $Ca_{0.05}Ce_{0.95}F_{2.95}$/Silicone Rubber Fluoride Electrode The ternary compound $Ca_{0.05}Ce_{0.95}F_{2.95}$ was prepared as described in Example 1 using a mixture of $CaF_2$ (5 mole percent) and $CeF_3$. Silicone rubber electrodes using this compound were prepared and tested as described in Example 1. Typical fluoride response is given in Table 4.

TABLE 4
FLUORIDE ION RESPONSE OF A $Ca_{0.05}Ce_{0.95}F_{2.95}$/SILICONE RUBBER FLUORIDE ELECTRODE

| $[F^-]$ | Potential, mV |
|---|---|
| $4.0 \times 10^{-5}$ | 255 |
| $1.2 \times 10^{-4}$ | 229 |
| $3.2 \times 10^{-4}$ | 205 |
| $7.2 \times 10^{-4}$ | 185 |
| $1.5 \times 10^{-3}$ | 165 |
| $3.4 \times 10^{-3}$ | 143 |
| $7.0 \times 10^{-3}$ | 125 |
| $1.3 \times 10^{-2}$ | 109 |
| Slope (mV/decade) | −58.4 |
| Resistance (ohms) | $2.4 \times 10^9$ |

EXAMPLE 5

Preparation of a $Ca_{0.10}Pr_{0.90}F_{2.90}$/Silicone Rubber Fluoride Electrode The ternary compound $Ca_{0.10}Pr_{0.90}F_{2.90}$ was prepared as described in Example 1 using a mixture of $CaF_2$ (10 mol percent) and $PrF_3$. Silicone rubber electrodes using this compound were prepared and tested as described in Example 1. Typical fluoride response is given in Table 5.

TABLE 5
RESPONSE OF $Ca_{0.10}Pr_{0.90}F_{2.90}$/SILICONE RUBBER FLUORIDE ELECTRODE

| $[F^-]$ | Potential, mV |
|---|---|
| $4.0 \times 10^{-5}$ | 247 |
| $1.2 \times 10^{-4}$ | 227 |
| $3.2 \times 10^{-4}$ | 206 |
| $7.2 \times 10^{-4}$ | 188 |
| $1.5 \times 10^{-3}$ | 171 |
| $3.4 \times 10^{-3}$ | 152 |
| $7.0 \times 10^{-3}$ | 134 |
| $1.3 \times 10^{-2}$ | 118 |
| Slope (mV/decade) | −51.5 |
| Resistance (ohms) | $1.3 \times 10^8$ |

EXAMPLE 6

Preparation of a $Ca_{0.10}Nd_{0.90}F_{2.90}$/Silicone Rubber FLuoride Electrode The ternary compound $Ca_{0.10}Nd_{0.90}F_{2.90}$ was prepared as described in Example 1 using a mixture of $CaF_2$ (10 mole percent) and $NdF_3$. Silicone rubber electrodes using this compound were prepared and tested as described in Example 1. Typical fluoride response is shown in Table 6.

TABLE 6
RESPONSE OF $Ca_{0.10}Nd_{0.90}F_{2.95}$/SILICONE RUBBER FLUORIDE ELECTRODE

| $[F^-]$ | Potential, mV |
|---|---|
| $4.0 \times 10^{-5}$ | 259 |
| $1.2 \times 10^{-4}$ | 237 |
| $3.2 \times 10^{-4}$ | 215 |
| $7.2 \times 10^{-4}$ | 198 |
| $1.5 \times 10^{-3}$ | 179 |
| $3.4 \times 10^{-3}$ | 158 |
| $7.0 \times 10^{-3}$ | 140 |
| $1.3 \times 10^{-2}$ | 125 |
| Slope (mV/decade) | −53.8 |
| Resistance (ohms) | $1.7 \times 10^8$ |

EXAMPLE 7

Preparation of a $Sr_{0.05}La_{0.05}F_{2.95}$/Silicone Rubber Fluoride Electrode The ternary compound $Sr_{0.05}La_{0.95}F_{2.95}$ was prepared as described in Example 1 using a mixture of $SrF_2$ (5 mole percent) and $LaF_3$. Silicone rubber electrodes using this compound were prepared and tested as described in Example 1. Typical fluoride response is given in Table 7.

TABLE 7
RESPONSE OF $Sr_{0.05}La_{0.95}F_{2.95}$/SILICONE RUBBER FLUORIDE ELECTRODE

| $[F^-]$ | Potential, mV |
|---|---|
| $4.0 \times 10^{-5}$ | 277 |
| $1.2 \times 10^{-4}$ | 255 |
| $3.2 \times 10^{-4}$ | 233 |
| $7.2 \times 10^{-4}$ | 213 |
| $1.5 \times 10^{-3}$ | 195 |
| $3.4 \times 10^{-3}$ | 174 |
| $7.0 \times 10^{-3}$ | 156 |
| $1.3 \times 10^{-2}$ | 140 |
| Slope (mV/decade) | −55.0 |
| Resistance (ohms) | $2.5 \times 10^8$ |

The selectivity of the $Sr_{0.05}La_{0.95}F_{2.95}$/silicone rubber fluoride electrode was investigated as follows. The fluoride electrode and the reference electrode were placed into TISAB solution containing a high concentration of the interfering ion, typically 0.1 M. For hydroxide interference studies, the pH of the TISAB buffer was adjusted to 10. The phosphate selectivity coefficient was determined in phosphate buffer containing a total phosphate concentration of 0.01 M. Additions of 0.01 M NaF were made and the steady-state potentials were recorded. The selectivity coefficient was calculated from the ratio of the fluoride ion concentration at which the response curve levels off (the lower detection limit) to the concentration of the interfering ion. The selectivity ratios are given in Table 8. The selectivity of this superionic fluoride ion conductor-based electrode is comparable to that of the single-crystal fluoride electrode.

TABLE 8
SELECTIVITY COEFFICIENTS FOR THE
$Sr_{0.05}La_{0.95}F_{2.95}$/SILICONE RUBBER
FLUORIDE ELECTRODE

| ION | SELECTIVITY |
| --- | --- |
| Nitrate | $4 \times 10^{-5}$ |
| Iodide | $5 \times 10^{-5}$ |
| Bromide | $5 \times 10^{-5}$ |
| Sulfate | $3 \times 10^{-5}$ |
| Chloride | $<5 \times 10^{-5}$ |
| Hydroxide | $1 \times 10^{-1}$ |
| Phosphate | $4 \times 10^{-4}$ |

EXAMPLE 8

Preparation of a Solid State $Sr_{0.05}La_{0.85}F_{2.85}$/Silicone Rubber

Fluoride Electrode

The $Sr_{0.15}La_{0.85}F_{2.85}$/silicone rubber electrode was prepared as described in Example 2, except that the internal solution was replaced with a solid-state contact. A saturated solution of AgF was prepared in methanol. After centrifugation, three drops of the supernatant were added to the inside surface of the silicone rubber membrane. The methanol was evaporated under vacuum in a desiccator for 2 hours. The electrode body was then packed with a silver-containing silicone rubber (Ecobond SLDR-59C). A coaxial cable was inserted into the silver/silicone rubber and the silicone rubber was allowed to cure overnight. The fluoride response of the resulting electrode was tested as described in Example 1. Typical response is shown in Table 9.

TABLE 9
RESPONSE OF SOLID STATE
$Sr_{0.15}La_{0.85}F_{2.85}$/SILICONE RUBBER
FLUORIDE ELECTRODE

| [F$^-$] | Potential, mV |
| --- | --- |
| $4.0 \times 10^{-5}$ | 828 |
| $1.2 \times 10^{-4}$ | 802 |
| $3.2 \times 10^{-4}$ | 780 |
| $7.2 \times 10^{-4}$ | 748 |
| $1.5 \times 10^{-3}$ | 738 |
| $3.4 \times 10^{-3}$ | 718 |
| $7.0 \times 10^{-3}$ | 702 |
| $1.3 \times 10^{-2}$ | 688 |
| Slope (mV/decade) | −56.4 |
| Resistance (ohms) | $5.0 \times 10^9$ |

EXAMPLE 9

Preparation of a Solid State, Planar $Sr_{0.05}La_{0.95}F_{2.95}$/Silicone

Rubber Fluoride Electrode

A planar fluoride electrode was prepared by forming the $Sr_{0.05}La_{0.95}F_{2.95}$/silicone rubber membrane in a small hole in a silastic sheet. A reinforced sheet of silicone rubber (Silastic Sheeting, medical grade RV, 40 mils thick) was cut into approximately 1 inch squares and a 5 mm diameter hole was punched in the center of the lower portion. The square sheet was placed on a "Lucite" block and the hole was filled with $Sr_{0.05}La_{0.95}F_{2.95}$/ Siloprene mixture, prepared as described in Example 7. Any excess mixture was removed and a "Lucite" block was placed on top of the silastic square, so that it was sandwiched between the two blocks. The Siloprene was allowed to cure at room temperature, in a press under slight pressure for at least 30 minutes, as described in Example 1. After this time, the silastic square was removed from the "Lucite"-blocks. One to three drops of the supernatant of a saturated solution of AgF in methanol, as described in Example 8, was added to one side of the $Sr_{0.05}La_{0.95}F_{2.95}$/silicone rubber membrane. The methanol was evaporated under vacuum in a desiccator for 1 hour. Then, a keyhole pattern was painted over the AgF treated side of the membrane using silver-containing silicone rubber (Ecobond SLDR-59C), so that the electrode membrane was completely covered and a narrow strip of the silver-containing silicone rubber extended to the top of the silastic square. After curing of the silver-containing silicone rubber for 1 hour under vacuum, the bottom portion was covered with cross-linked Siloprene K1000, leaving only a small portion at the top of the square exposed to make electrical connection. The Siloprene was cured for 1 hour under vacuum. To test the response of the planar fluoride electrode. 0.1 mL of the test solution, prepared in TISAB, was placed on top of the electrode membrane (the untreated side). A miniature Ag/AgCL electrode, positioned above the fluoride electrode, served as the reference electrode. Typical response is shown in Table 10.

TABLE 10
RESPONSE OF SOLID STATE PLANAR
SILICONE RUBBER FLUORIDE ELECTRODE

| [F$^-$] | Potential, mV |
| --- | --- |
| $4.0 \times 10^{-5}$ | 786 |
| $4.4 \times 10^{-4}$ | 734 |
| $4.2 \times 10^{-3}$ | 674 |
| $3.1 \times 10^{-2}$ | 620 |
| Slope (mV/decade) | −57.7 |
| Resistance (ohms) | $5.3 \times 10^9$ |

What is claimed is:

1. A membrane having an active component for use in fluoride ion-selective electrodes, the active component comprising a ternary compound of the type, $M_xLn_yF_{3-x}$ where M is an alkaline earth metal ion and Ln is a lanthanide metal ion, and y equals $1-x$;
   where the alkaline earth metal is selected from the group consisting of calcium, strontium and barium,
   where the lanthanide metal is selected from the group consisting of lanthanum, cerium, prosiodymium, neodymium, promethium, samarium and europium, and
   where the membrane is a hydrophobic polymer matrix and the ternary compound is in the form of particles disposed throughout the matrix.

2. A membrane having an active component for use in fluoride ion-selective electrodes, the active component comprising a ternary compound of the type, $M_xLn_yF_{3-x}$ where M is an alkaline earth metal ion and Ln is a lanthanide metal ion, and y equals $1-x$; and where the membrane is a hydrophobic polymer matrix and the ternary compound is in the form of particles disposed throughout the matrix.

3. The membrane set forth in claim 2 wherein the particles have a diameter of less than 75 $\mu$m and comprise 50 to 90% w/w of the matrix.

4. In a fluoride ion-selective electrode for determining the concentration of fluoride ions in a solution to be measured, the electrode having a tube adapted to contain an internal reference solution containing fluoride ions, an internal reference electrode positioned in the tube and adopted to be contacted by the solution, and a diffusion membrane at one end of the tube adopted to function as a diffusion barrier between the solution to be measured and the reference solution, the improvement wherein the membrane comprises a ternary compound of the type, $M_xLn_yF_{3-x}$ M is an alkaline earth metal ion and Ln is a lanthanide metal ion, as the active component, and y equals $1-x$;

the membrane being a hydrophobic polymer matrix and the ternary compound being in the form of particles disposed throughout the matrix.

5. The electrode as claimed in claim 4 wherein the particles have a diameter of less than 75 $\mu$m and comprise 50 to 90% w/w of the matrix.

6. A method for making a fluoride ion-selective electrode for determining the concentration of fluoride ions in a solution to be measured, the electrode having a tube adapted to contain an internal reference solution containing fluoride ions, an internal reference electrode positioned in the tube and adapted to be contacted by the solution, and a diffusion membrane at one end of the tube adapted to function as a diffusion barrier between the solution to be measured and the reference solution, the improvement wherein the membrane is prepared by the steps of: forming a ternary compound of the type, $M_xLn_yF_{3-x}$ where M is an alkaline earth metal ion and Ln is a lanthanide metal ion, grinding the ternary compound into particles, and incorporating the particles into a hydrophobic polymer to form a matrix of particles and y equals $1-x$.

7. The method of claim 6 wherein the particles have a diameter of less than 75 $\mu$m and comprise 50 to 90% w/w of the matrix.

8. The method of claim 7 wherein the ternary compound is $M_{0.05}Ln_{0.95}F_{2.95}$, where M is an alkaline earth metal ion and the lanthandine metal is selected from the group consisting of lanthanum, cerium, prosiodymium, neodymium, promethium, samarium and europium.

9. The method of claim 8 wherein the particle size is less than 40 $\mu$m.

10. The method of claim 9 wherein the polymer is silicone rubber.

* * * * *